US009289158B2

(12) United States Patent
Pfeiffer et al.

(10) Patent No.: US 9,289,158 B2
(45) Date of Patent: Mar. 22, 2016

(54) CALIBRATION-FREE AND PRECISE OPTICAL DETECTION OF A THREE-DIMENSIONAL SHAPE

(75) Inventors: Rene Pfeiffer, Markgroningen (DE); Dirk Rutschmann, Stuttgart (DE)

(73) Assignee: CORPUS.E AG, Stuttgart (DE)

( * ) Notice: Subject to any disclaimer, the term of this patent is extended or adjusted under 35 U.S.C. 154(b) by 491 days.

(21) Appl. No.: 13/518,491

(22) PCT Filed: Jan. 27, 2010

(86) PCT No.: PCT/EP2010/000479
§ 371 (c)(1),
(2), (4) Date: Aug. 31, 2012

(87) PCT Pub. No.: WO2011/076292
PCT Pub. Date: Jun. 30, 2011

(65) Prior Publication Data
US 2013/0053702 A1 Feb. 28, 2013

(30) Foreign Application Priority Data
Dec. 22, 2009 (DE) ...................... 20 2009 017 401 U

(51) Int. Cl.
*A61B 5/107* (2006.01)
*A61B 5/00* (2006.01)
*G01B 11/25* (2006.01)
*A61B 5/103* (2006.01)

(52) U.S. Cl.
CPC ............. *A61B 5/1077* (2013.01); *A61B 5/0064* (2013.01); *A61B 5/1079* (2013.01); *A61B 5/415* (2013.01); *G01B 11/25* (2013.01)

(58) Field of Classification Search
CPC .... A61B 5/0064; A61B 5/1077; A61B 5/415; A61B 5/1079; G01B 11/25
See application file for complete search history.

(56) References Cited

U.S. PATENT DOCUMENTS

| 3,690,242 A | 9/1972 | Cruickshank |
| 7,241,045 B2* | 7/2007 | Skalli et al. ................... 378/207 |
| 7,489,813 B2 | 2/2009 | Rutschmann et al. |
| 2004/0125205 A1* | 7/2004 | Geng ........................... 348/142 |

(Continued)

OTHER PUBLICATIONS

D'Apuzzo. Electronic Imaging 2006, San Jose, CA. Jan. 16, 2006.*
Knyaz. "Automated Calibration Technique for Photogrammetric System Based on a Multi-Media Projector and a CCD Camera" Proceedings of the ISPRS Commission V Symposium 'Image Engineering and Vision Metrology'. 2006.*

(Continued)

*Primary Examiner* — Long V Le
*Assistant Examiner* — Colin T Sakamoto
(74) *Attorney, Agent, or Firm* — Carlson, Gaskey & Olds, PC

(57) ABSTRACT

A support plate with a horizontal flat standing surface carries two posts, and is rotated about a vertical axis. A stationary triangulation measuring head having a camera and a light line projector, projects light lines, which are perpendicular to the plane of the support plate, onto a person who stands upright on the standing surface of the plate. Encoded, photogrammetrically evaluatable marks are arranged on the plate around the standing surface and on the post. Images taken by the camera during rotation of the plate are transferred to a computer to determine a three-dimensional shape of the person or of part of the person. Marking-free fields are arranged on the support plate and on the post. The computer determines the parameters of the triangulation measuring head to performs a self-calibration of the detection process based on positions of the photogrammetric marks and shapes of light traces on the marking-free fields.

22 Claims, 6 Drawing Sheets

(56) References Cited

U.S. PATENT DOCUMENTS

| | | | |
|---|---|---|---|
| 2004/0202364 A1* | 10/2004 | Otani et al. | 382/154 |
| 2004/0227751 A1* | 11/2004 | Anders | 345/419 |
| 2004/0234122 A1 | 11/2004 | Kochi et al. | |
| 2006/0140463 A1* | 6/2006 | Rutschmann | 382/128 |
| 2010/0296726 A1 | 11/2010 | Rutschmann et al. | |

OTHER PUBLICATIONS

Li. "Reconstruction Using Structured Light" Karlsruhe Institute of Technology, formerly known as Universitat Karlsruhe. 2004.*

Translation of International Preliminary Report on Patentability (Mar. 23, 2012).

* cited by examiner

CALIBRATION-FREE AND PRECISE OPTICAL DETECTION OF A THREE-DIMENSIONAL SHAPE

TECHNICAL FIELD

The present invention relates to a method and apparatus for calibration-free, cost-efficient and precise optical detection of the three-dimensional shape of a body or body part.

BACKGROUND OF THE INVENTION

The detection of the three-dimensional spatial shape of bodies or body parts, in particular of human body parts, such as legs, torso or feet, is an important aspect in the production or assignment of fitting articles of clothing, orthopedic aids such as compression stockings, prostheses and ortheses and also in the production or assignment of fitting shoes. In addition, such body scanners are also made use of more and more frequently in the form of whole-body scanners in the field of medical diagnosis of orthopedic results such as scoliosis of the back, of therapy monitoring of lymphedemas, and of cosmetic surgical procedures such as liposuction etc.

All of these applications require "real" 3D scanners, i.e. scanners which are capable of detecting a complete 3D model both of the convex and the concave parts of the body. Therefore, in considering the prior art, pseudo 3D methods such as the silhouette method (taking images of the silhouette of a body from several directions) are excluded since these methods are not normally able to provide a complete 3D model.

The users of scanners rightly expect, for cost reasons, that the same body scanner can be utilized as far as possible for different areas of application and different tasks and that the 3D data required for a particular application is taken as a subset from the complete 3D data set prepared of the entire body. It is only in this way that an uneconomic split-up of the tasks set to a large number of specific scanners such as foot scanners, back scanners, torso scanners, knee scanners, shoulder scanners etc. can be avoided.

This demand for a whole-body scanner places high requirements on the measuring room (area of approx. 1 m²×height of 2 m) to be covered by these scanners, the necessary high resolution of typically 1000 spatial points per cubic centimeter, and the high precision of the 3D model prepared of approx. 0.5 mm, a precision that is, above all, constant in the long term.

In addition to these rather technical specifications, these whole-body scanners are required to satisfy a number of further conditions in order to be economically successfully employed in those areas that are very critical in terms of cost, i.e. in the medical field, the paramedical and sanitary medical industries, and in mass customization of clothing and protective clothing:

(a) the body scanner needs to manage with as small a floor space as possible because the space available is often very limited;

(b) the body scanner needs to be able to operate under normal ambient light conditions, i.e. without being installed in a dark and separated booth, because this leads to anxieties and reluctance in many customers;

(c) the body scanner needs to be able to be reliably operated even by staff who have received only little training. This makes it absolutely necessary to avoid any frequent and complicated recalibration processes, which would ask too much of such staff;

(d) in spite of these high requirements, manufacturing costs and operating costs must be very low to allow an application in the above-mentioned cost-sensitive fields of business.

Meanwhile, numerous optical 3D body scanners are on the market, most of which operate either on the basis of the methods of laser light section (see, e.g., Vitronic Dr. Stein, www.http://www.vitronic.de/bodyscannen) or stripe projection (see, e.g., bodyScan of Breuckmann, www.breuckmann.com). Both methods are based on triangulation, i.e. a very stable and precise spatial triangular arrangement of a light projector, a camera and a body for point-by-point determination of the distance of the body surface observed from the camera/projector measuring head. An XYZ point model of the body surface viewed is prepared from the sum of this distance data in a world-related and/or object-related coordinate system. In further processing steps, a 3D model suitable for the further processing is calculated therefrom, in most cases by a triangulated mesh, in any one of the numerous standardized formats such as .dxf, VRML, STEP etc.

In order to detect the entire body, either a plurality of camera/projector arrangements need to be mounted around the body (e.g., in the case of the bodyScan of Breuckmann) or a plurality of camera/projector arrangements need to be mechanically moved over the body surface (e.g., in the case of the VITUS whole-body scanner of Vitronic Dr. Stein).

A detailed presentation of the currently commercially available body scanners and the technologies made use of can be found via the Internet portal www.hometrica.ch.

The required angular arrangement of the camera relative to the projector is sensitive: even small angle errors result in large errors of measurement in the distances measured. The movement of the camera/projector arrangement in the space is equally sensitive: small errors in the position determination of the measuring head while an image is taken result in large errors of measurement in the 3D model generated. This sensitivity results in that, even in the case of a very sturdy and expensive opto-mechanical construction, all scanners using the principle of triangulation still require frequent recalibration, in particular also after each transportation and upon each movement of the scanner.

The necessary recalibration of a 3D scanner operating on the basis of triangulation using laser or stripe projection requires various standards such as standard bodies, marked plates etc., and generates a large number of parameters which are required in order to ensure the measuring accuracy. These include:

the exact spatial position between the camera and the projector (triangulation angle, base line, mutual orientation, etc.);

the exact internal parameters of the camera and the projector (focal lengths, sensor dimension, geometry of the picture elements, tilt angle and angle of rotation of the laser line projector, etc.);

the exact spatial positions of the camera/projector measuring head for each measuring image taken, the so-called external parameters; etc.

Therefore, as a rule, recalibration of a 3D scanner is a complicated process which in many cases is asking too much of the sales staff of, e.g., an orthopedic specialist store, who therefore tend not to accept this technology.

Because of the mechanical stability required, today's 3D whole-body scanners based on triangulation cannot be offered at a particularly low price, either, so that currently many potential applications are not commercially put to practice due to the high costs of the 3D scanners.

The company of corpus.e AG (www.corpus-e.com) has developed a photogrammetric foot scanner under the name "Lightbeam®", which operates without a projector and without a sensitive triangulation arrangement (see www.corpus-e.com). The foot is covered with a specially photogrammetrically marked, elastic sock here and a video camera is mechanically moved around the foot (see WO 2004/078040 A1).

The foot is placed on a photogrammetrically marked support, so that the spatial position from which the camera measures can be permanently and automatically determined using the methods of photogrammetry (the so-called "external" parameters of a photogrammetric measuring arrangement). Likewise, the so-called "internal" parameters of the camera itself, such as focal length, image sensor, piercing point of the optical axis, lens distortions, etc. can be determined automatically from the evaluation of overlapping 2D images taken of the marked support and the marked foot. This makes this system completely calibration-free or, more precisely, inherently self-calibrating. It may be put into operation after transportation at any time without calibration by the user; there is no need to ever recalibrate it after a change of load; the design may be simple and inexpensive in terms of mechanical stability since the latter does not contribute to the final result, the 3D model measured.

However, this otherwise powerful method has a drawback: due to the density, which is limited owing to the textile nature, of the photogrammetric markings on the elastic sock, the density of the XYZ point cloud generated is distinctly lower in comparison with a laser or stripe projection method (typically 4000 XYZ points as against approx. 1 million XYZ points in the case of a light section scanner). While this lower point density does not constitute a disadvantage in the case of flat body parts such as the upper foot, it may be restricting in regions of high spatial curvatures such as in the region of the toes, the heel, the transition from the upper foot to the sole, etc.

DE 101 56 908 A1 also discloses a method of detecting the three-dimensional shape of a body, in which the body to be measured is completely covered with a photogrammetrically marked, elastic covering. The body is placed on a plate which includes photogrammetrically evaluatable marks. Overlapping images are taken freehand by an operator.

The requirement that the body to be measured needs to be completely covered with a photogrammetrically marked, elastic covering constitutes a further drawback. Such coverings are not simple to produce; depending on the physique of the customer and depending on the body part in question, such as the torso, legs, feet, shoulders, hands, etc., several shapes and sizes are necessary.

There are also scanning applications such as, e.g., the digitization of feet for the selection of suitable ski boots, in which it is important that the customer keeps on his/her own winter sock, for the sock to be taken into consideration in the shape adaptation. But it is not possible to photogrammetrically mark any random sock later using simple means.

Therefore, despite the freedom from calibration achieved, this system is not particularly suitable for a low-cost whole-body scanner.

DE 196536294 A1 to Malz et al. describes a general method of 3D digitization of objects with the aid of a camera/light projector triangulation arrangement in which the entire measuring room is provided with photogrammetrically marked side walls and, in addition, further photogrammetrically marked calibration bodies are placed in the measuring room. This method allows the explicit in situ calibration of the measuring arrangement.

This methodology is applicable in a measuring laboratory where well-trained staff digitize primarily rigid mechanical models such as, e.g., in automotive engineering. It is, however, not very suitable for a low-cost whole-body scanner in which the number of photogrammetrically marked surfaces in a measuring booth of a medical supply store is intended to be small and, if possible, also aesthetically non-intrusive, where no calibration bodies or panels to be manually installed should be required at all and, altogether, the impression of a closed measuring room should be avoided. This method described by Malz is also not very suitable for a whole-body scanner which is to be used for digitizing the human body all around, i.e. completely from a large number of views and as quickly as possible.

In WO 2009/065418 A1 of 28 May 2009, Rutschmann and Pfeiffer present a body scanner which likewise manages without any photogrammetrically marked textile coverings while still maintaining the desired principle of freedom from calibration (or of implicit recalibration). This method uses a photogrammetrically marked base plate on which a customer stands, and a laser line/camera triangulation arrangement mechanically moved around the body approximately on a circular path. Here the camera is oriented in such a manner that for each position on the orbit it also covers a detail of the floor markings and, at a higher position roughly in the center of the image, likewise also covers an elastic, photogrammetrically marked band which is wrapped around the customer's leg, for example. With each exposure, the camera thus simultaneously detects the following elements:

the (at least one) bright light line of the laser projector on the body surface, which runs vertically through the image field;

the same line in the lower part of the image field, which generates a bright trace on the photogrammetric base plate;

the bright trace of the light line on the elastic band roughly in the center of the image.

Provided that the single design requirement is met that the laser line generated is straight, both the internal parameters of the camera and the external parameters of the line projector/camera measuring head (triangulation angle, base line, orientation in space) can be determined from the numerous images taken by the camera around the body using known photogrammetric methods. This makes this system inherently self-calibrating; any mechanical change to the critical components, that is, the line projector and the camera, i.e. all of the internal and external parameters are photogrammetrically determined at the same time with each digitization.

This results in a significant advantage to the user: these scanners need not be recalibrated by the user. To the manufacturer this inherent self-calibration means that no extremely rigid and precise designs, no complicated adjustments etc. are necessary, making such body scanners cost-efficient to produce and simple to put into operation at the customer's.

But even with all the advantages, the method described by Rutschmann et al. still has a number of drawbacks: Due to the movement of the camera/line projector arrangement around the body of the customer, a relatively large cylindrical space is required; such a scanner typically requires a circular area of about 3 m in diameter since minimum distances between the camera/laser measuring head and the body of the customer need to be observed. Medical supply stores and hospitals often do not dispose of spaces of such size, but expect a whole-body scanner which requires as little floor space as possible. The manual application of a photogrammetrically marked band or similar mark in the image field is a source of error and requires a certain degree of optical understanding; the sales staff often lack such understanding. In addition, WO 2009/065418 A1 does not solve the problem of realizing a whole-body scanner which reaches at least from the feet up to the shoulder/neck area. Even with extreme wide angle cameras, the camera/line projector arrangement shown is not able to illuminate the top surface of the shoulder with the line projector and to capture it optically simultaneously with the photogrammetrically marked floor plate, or to capture the occluded parts of the lower belly in an image.

WO 2009/065418 A1 does also not teach how to clearly recognize the light trace of the line projector among the multiplicity of the photogrammetric marks and how to evaluate it based on the image of the camera. Deviations from the design-related rectilinearity of the line projector are not recognized and cannot be corrected automatically.

There is therefore an economic and technical interest in a cost-efficient, calibration-free or inherently recalibrated body scanner that is simple to operate, for high-resolution detection of the anatomical three-dimensional shape mainly of human bodies, which does not require a photogrammetrically marked measuring textile, which manages with a small-volume measuring setup, and automatically generates a 3D model of such precision and density that it can be utilized for a multitude of applications ranging from medical and orthopedic fields to mass customization of footwear and clothing.

SUMMARY OF THE INVENTION

This object is achieved with the method indicated in the claims and with a detection arrangement indicated in the claims.

In one example, the customer stands on a rotary plate that is motor-driven or moved by hand. At least one light line, which is oriented substantially perpendicularly to a plane of the rotary plate is projected on the customer by a triangulation measuring head. Outside of a foot region, the flat rotary plate is provided with encoded, photogrammetrically evaluatable marks which are interrupted by at least one marking-free field. A further surface provided with encoded, photogrammetrically evaluatable marks is located substantially vertically above the rotary plate and preferably on posts or holding bars provided for the customer to hold onto during rotation of the rotary plate. This marked surface is also interrupted by at least one marking-free field. During the rotational movement of the body along with the rotary plate, all visible photogrammetric marks are recorded in the images respectively taken by the camera, as are the marking-free fields included therein, and in the triangulation measuring head the corresponding signals of the camera are continuously transferred to a computer. The position of the marking-free fields in relation to the surrounding or adjacent photogrammetric marks is known to the computer, e.g. in the form of a list or table of the marks which are boundary marks for the marking-free fields. Using a photogrammetric program, the light trace projected by the at least one light projector of the triangulation measuring head onto the body to be digitized is evaluated in all images to determine the 3D model of the body in accordance with known methods of triangulation. At the same time, the positions of the photogrammetric marks on the rotary plate and on the posts or holding bars, which the customer holds onto during rotation, are evaluated from a multitude of these images with the aid of a photogrammetric program. Further, the positions of the line-type light traces of the at least one line projector in the marking-free fields of the rotary plate and the holding bar are determined. All internal and external parameters of the at least one triangulation measuring head are determined from both evaluations with the aid of the above-mentioned photogrammetric program and are used for the inherent self-calibration of the 3D model. The course of the light trace on an unmarked field of the rotary plate in fact allows a derivation of the triangulation angle between the camera and the projected light plane in the XY-plane, i.e. in relation to the base area of the world coordinate system XYZ. For another thing, the course of the light trace on an unmarked field of the holding bars allows the cant of the line projector, i.e. the angle of rotation in the ZX-plane, to be determined. To this end, however, the position of the unmarked surface of the holding bar in space needs to be known. The position(s) of this/these non-marked surface(s) in space is/are established photogrammetrically from the images of the camera during the rotational movement with the aid of the absolute markings of the posts or holding bars. Deviations from the rectilinearity of the projected line, for example due to errors or misalignments of the beam shaping optical systems of the line projector, can be also calibrated in that a plurality of sections of the projected line on the largely vertically oriented, mark-free field of the holding bars or posts are detected by the camera or cameras of the measuring head and are described in a known manner by a function, e.g. a polynomial function. This non-linear light section function is then applied in the 3D reconstruction.

Specifically, a support plate on which a horizontal flat standing surface is formed, and which carries at least one substantially vertically projecting post, is rotated about a vertical axis. At least one stationary triangulation measuring head, including at least one camera and at least one light line projector, projects light lines that are substantially perpendicular to the plane of the support plate onto a person who stands upright on the standing surface of the support plate. Encoded, photogrammetrically evaluatable marks are arranged on the support plate around the standing surface and on the post or a substantially vertical structure connected with the support plate. The images captured by the camera during rotation of the support plate are transferred to a computer, and the computer determines the three-dimensional shape of the person or of part of the person by means of a photogrammetric program. In the process, at least one marking-free field is arranged on the support plate and at least one marking-free field is arranged on the post or the structure attached thereto. The positions of the marking-free fields relative to the photogrammetric marks are selected such that they can be uniquely determined on the basis of the photogrammetric marks. In particular, the marking-free fields are surrounded by or adjacent to the photogrammetric marks. The positions of the marking-free fields relative to the surrounding or adjacent photogrammetric marks is known to the computer, e.g. in the form of a list or table of the marks which are boundary marks for the marking-free fields. On the basis of the positions of the photogrammetric marks and the positions and shapes of the light traces on the marking-free fields, the computer determines the parameters of the triangulation measuring head and in this way performs a self-calibration of the detection process.

When using a plurality of triangulation measuring heads, a measuring space from the support plate at least up to the highest point to be detected of the person's body is covered, each with an overlap, each triangulation measuring head being oriented such that it detects at least part of the marks of the support plate and of the post or the structure connected therewith.

Advantageously, the line projectors of a plurality of triangulation measuring heads illuminate the person in different spectral regions and the respectively associated camera only detects light from this spectral region through an optical filter.

In particular, the line projectors of a plurality of triangulation measuring heads illuminate the person in different spectral regions and the computer allocates the light traces of the individual line projectors in the image of the associated color-capable camera to the line projectors by means of a color classification program.

A further option provides that the line projectors of the plurality of triangulation measuring heads are turned on at different times for short periods of time with a pulsing device, and a synchronizing device synchronizes these time periods with the image change of the cameras.

BRIEF DESCRIPTION OF THE DRAWINGS

Further details of the invention will be apparent from the following detailed description with reference to the accompanying drawings, in which.

DETAILED DESCRIPTION

Figure 1:
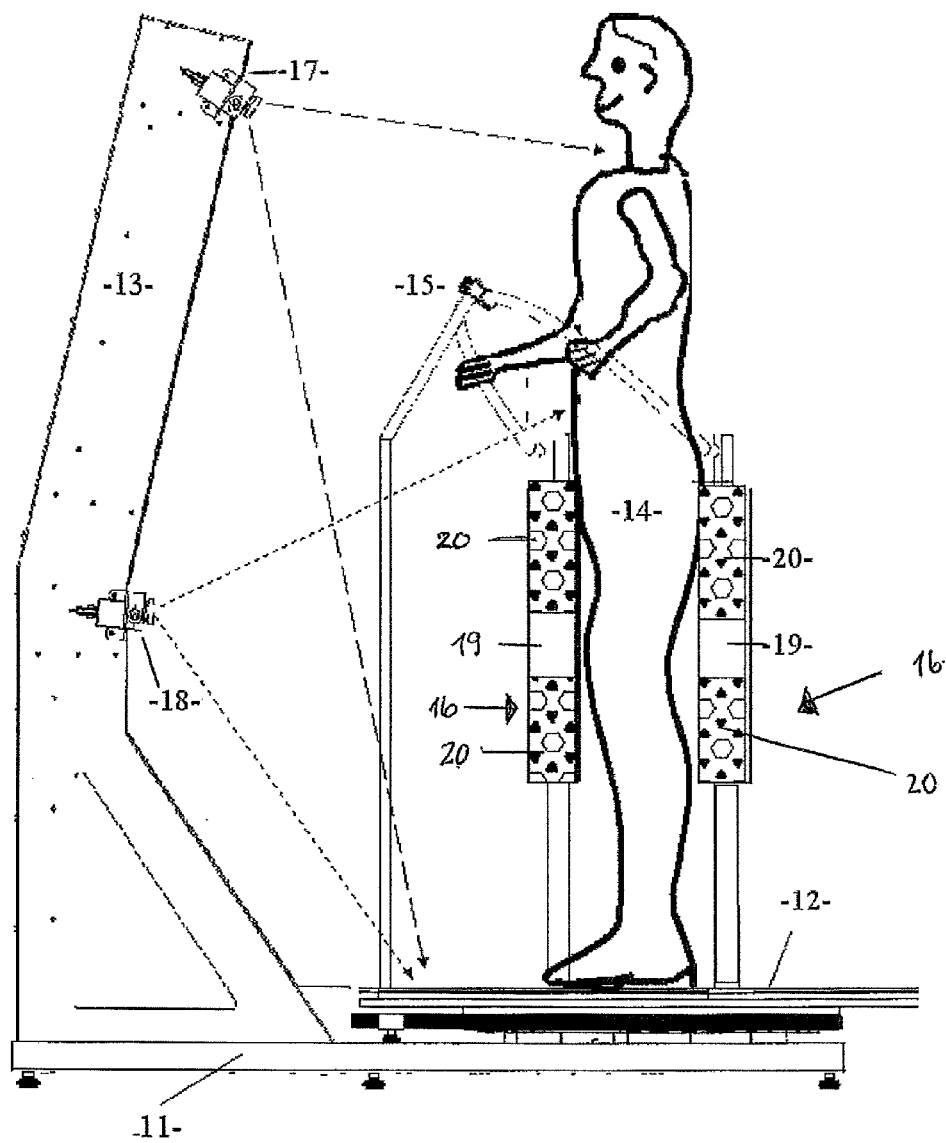
FIG. 1 shows a schematic side view of a 3D detection arrangement in use.

FIG. 1 shows, in a simplified illustration, the mechanical-optical setup of a detection arrangement 11, which comprises a circular, flat and preferably motor-driven support plate 12 having a standing surface around which the support plate is provided with photogrammetric marks in a special manner. A customer 14 stands upright on this standing surface of the support plate, also referred to as a "rotary plate" below. A holding device which the customer 14 holds onto during the rotational movement comprises a holding bow 15 and two posts 16 projecting vertically from the rotary plate. The arrangement further includes a measuring arm 13 which orients, e.g., two camera/laser line projector measuring heads 17, 18 such that the heads detect both a part of the body of the customer 14 and a part of the rotating photogrammetrically marked surface of the rotary plate 12. The posts 16 are likewise provided with photogrammetric marks in a special manner. This marking comprises two partial surfaces 20 with photogrammetrically evaluatable marks and a mark-free partial surface 19. Rather than the posts 16, other structures may be used which are substantially vertical and rigidly connected with the support plate 12 or the posts 16, for the partial surfaces 20 with photogrammetrically evaluatable marks and the mark-free partial surface 19 to be arranged thereon.

Figure 2:
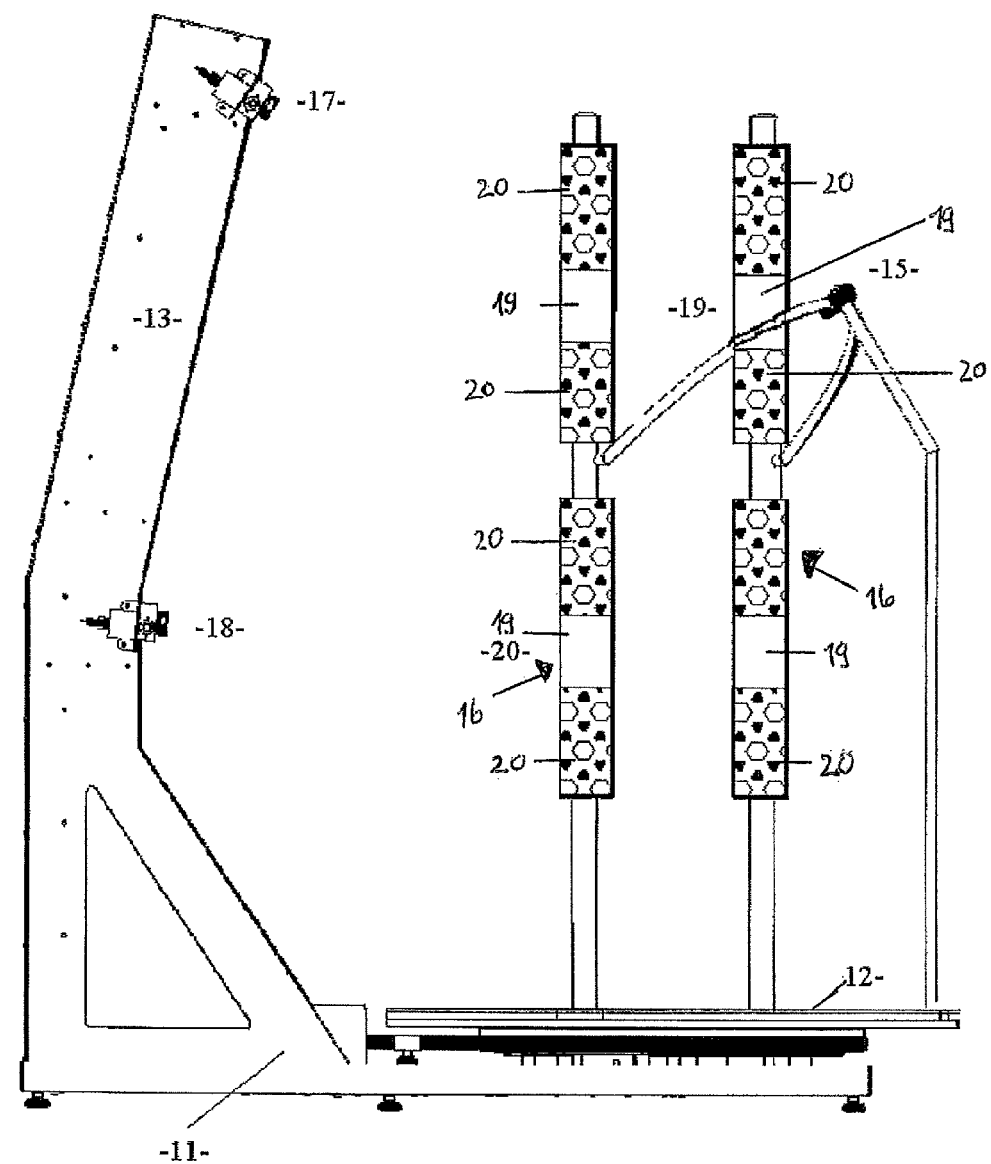
FIG. 2 shows a schematic side view of a further development of the 3D detection arrangement.

FIG. 2 shows a variant of the basic setup of FIG. 1, in which the photogrammetric marking of the posts 16 is repeated above the waist of the customer 14, to detect advantageously placed photogrammetric marks for the inherent self-calibration according to the invention, particularly of the upper camera/laser line measuring head 17.

Figure 3:
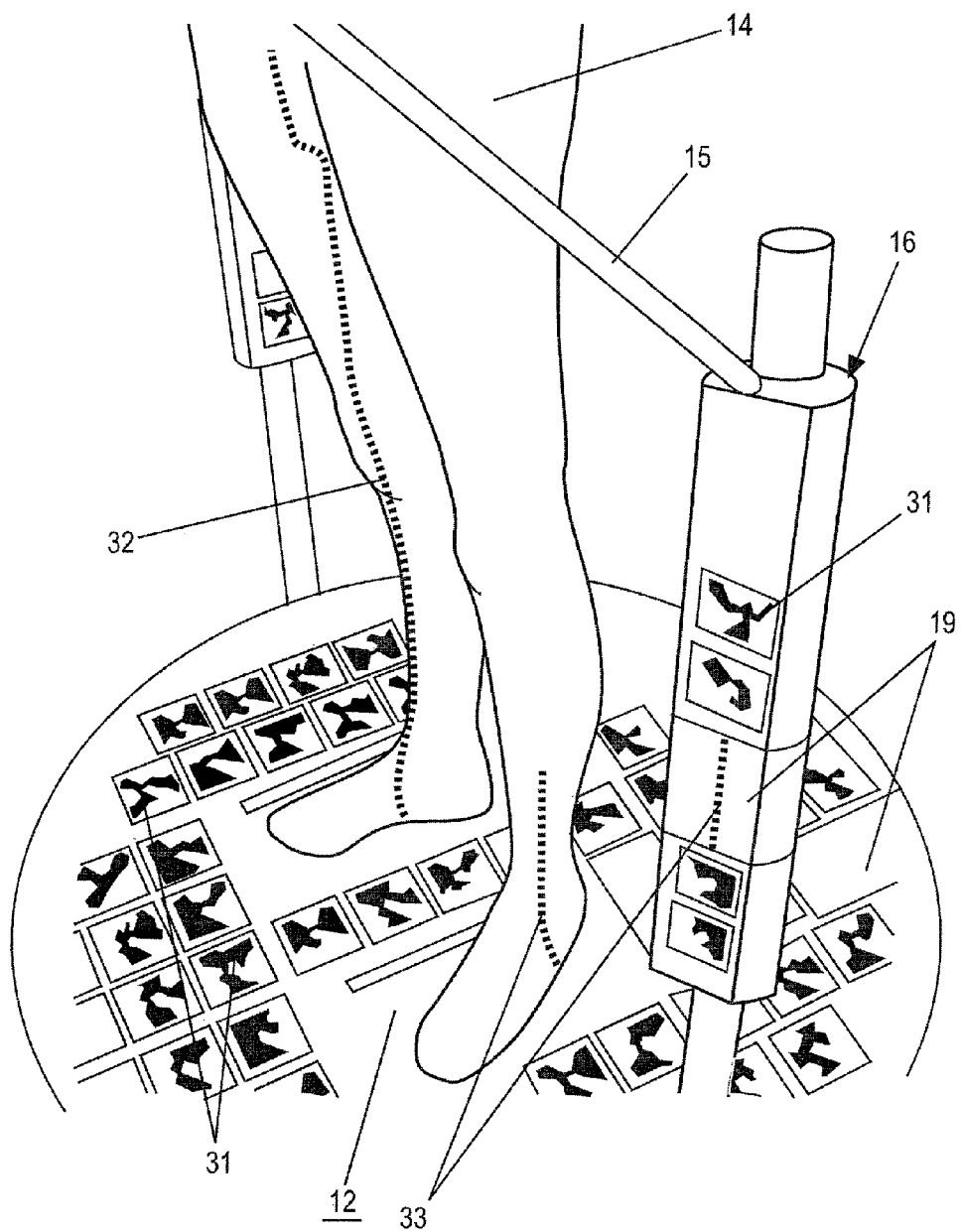
FIG. 3 shows a perspective oblique view to illustrate a detection process.

FIG. 3 shows a top view of the photogrammetrically marked base area of the rotary plate 12 and of the marking of the post 16, with two fundamentally different types of markings according to the invention being visible, namely, a larger number of absolutely encoded photogrammetrically evaluatable marks 31 and some free, markless fields 19 within the fields of photogrammetric marks; in these free fields 19 the course of the light traces of the line projector or projectors is recognizable undisturbed by marks. In addition, by way of example the light trace 32 of a line projector of the measuring head is indicated on the right leg, and part of the light trace 33 of a second line projector is indicated on the left foot and calf region.

Figure 4:
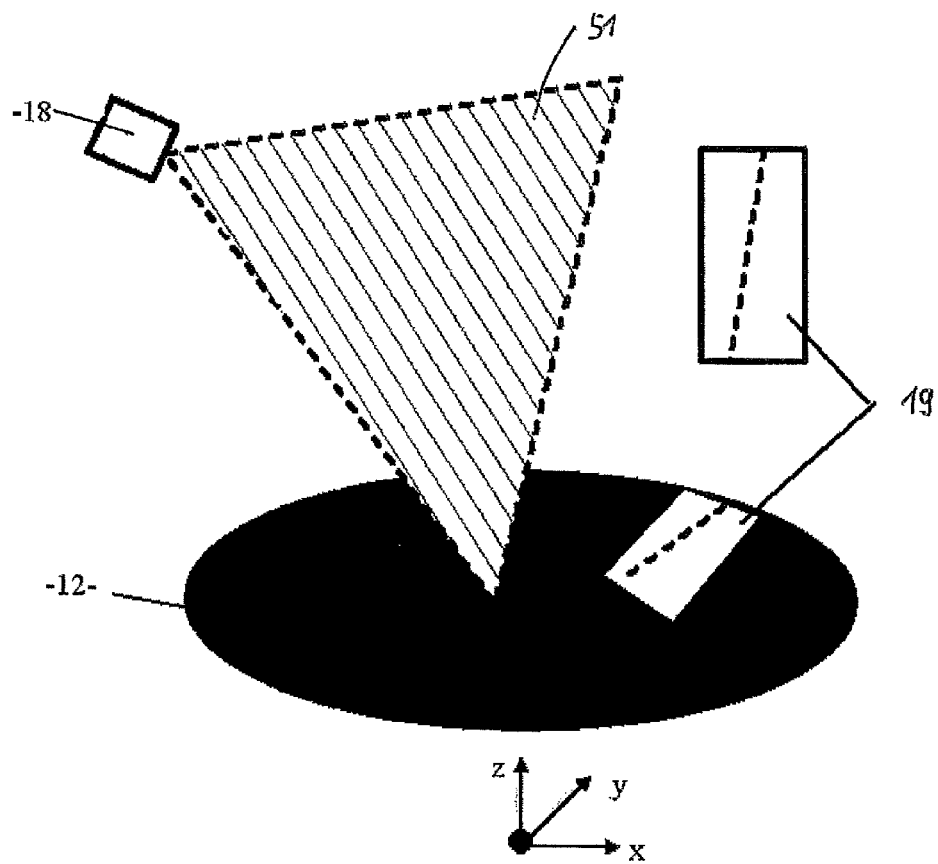
FIG. 4 shows a sketch to explain an aspect of the inherent calibration.

FIG. 4 shows, in a sketch reduced to the essential elements, the triangulation measuring head 18, the photogrammetrically marked (shown in black), motor-driven rotary plate 12, and a projected light plane 51. This sketch clearly illustrates how, based on the course of the light traces of the line projector, the rotation of the line projector in the XY-plane is visible in the non-marked field of the rotary plate bordered by photogrammetric marks, and the cant of the line projector in the ZX-plane is visible in the vertical, non-marked bright field of the post bordered by photogrammetric marks, and thus the rotation and the cant are evaluatable from the image of the camera, therefore providing all data for automatically photogrammetrically determining the internal and external parameters of the triangulation arrangement of the camera and the line projector and thus for configuring the entire measuring head to be inherently recalibratable.

Figure 5:
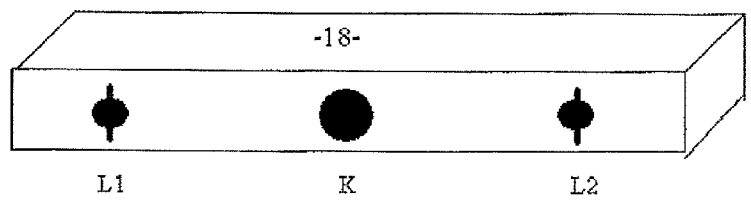
FIG. 5 shows a schematic perspective view of a triangulation measuring head.

FIG. 5 shows an exemplary measuring head 18, comprising a camera K and a pair of light line projectors L1 and L2 which are symmetrically mounted to the right and left thereof at a base distance d and continuously illuminate the measuring space with these line structures.

Figure 6:
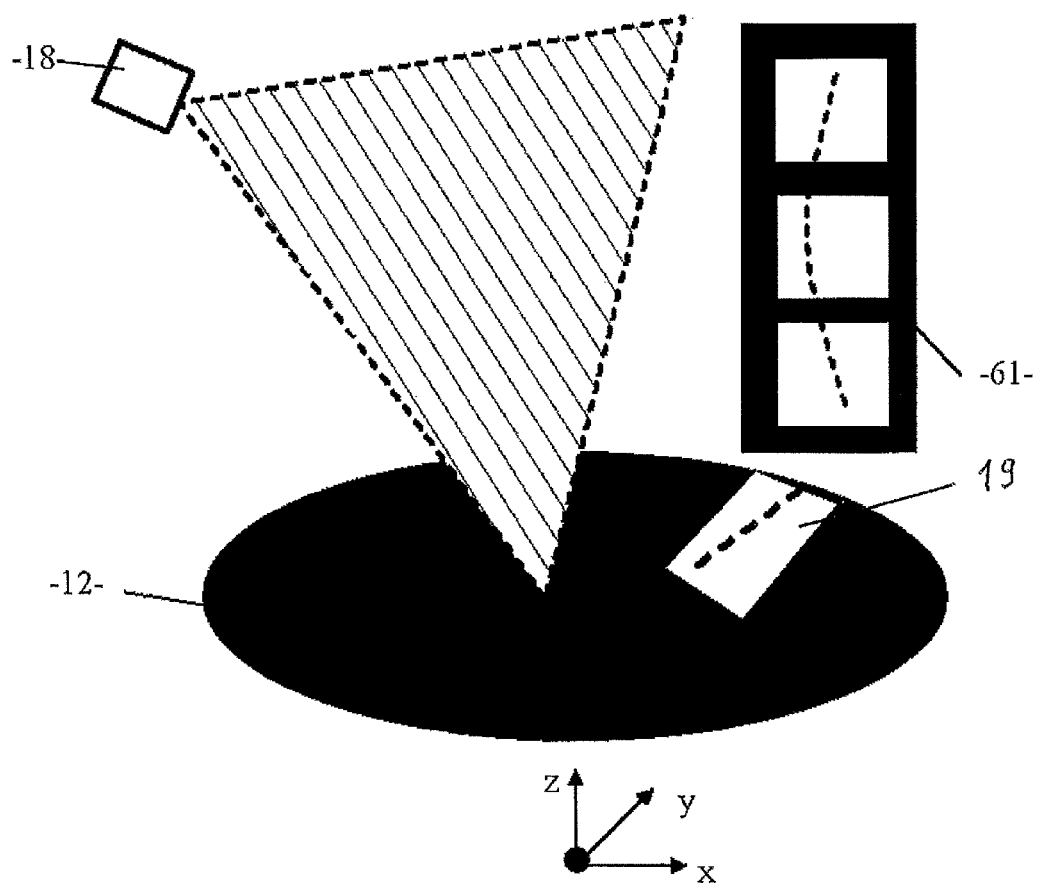
FIG. 6 shows a further sketch to explain a different aspect of the inherent calibration.

FIG. 6 shows, by way of example, how deviations from the rectilinearity of the line projector are also recognized in that substantial sections of the light trace projected on the mark-free surface 61 that is predominantly arranged vertically and bordered by markings are recorded with the camera in the measuring head 18 and the non-rectilinear course is modeled by a smooth approximation function such as, e.g., a polynomial function.

The concept of the invention will now be described with reference to an arrangement which relates to a whole-body scanner, including a measuring space which extends from the feet to the neck region of the customer and operating with two vertically stacked triangulation measuring heads. By way of example and as seen in the sketch of FIG. 4, these each comprise a camera K and a pair of vertically emitting line projectors L1 and L2 arranged to the right and left at a distance d therefrom. This special design is selected for didactic reasons and is not to be construed in a limiting sense. The concept of the invention also comprises body scanners having a different, smaller or larger image field or having only one single, or else more than two, triangulation measuring heads, or having triangulation measuring heads with more than one camera, and/or more than two line projectors.

Triangulation measuring heads of this type are known to those of ordinary skill in the art of image processing. As a rule, semiconductor lasers are made use of as line projectors, having an optical system placed in front for producing a straight-line light trace that is defined as sharply as possible.

As shown in FIG. 1, the calibration-free or inherently self-calibrating (both terms are used as synonyms in connection with this description) detection arrangement 11 in one example includes the following basic elements:

(1) a rigid mechanical structure for receiving a motor-driven rotary plate 12 on which the customer 14 to be scanned stands upright and holds on to a holding bow 15, a holding structure or arm 13 for receiving and rigidly orienting, e.g., two triangulation measuring heads 17, 18 (camera/laser line projector), the scanning spaces of which are oriented such that they partially overlap and that they both detect a partial portion of the photogrammetrically marked rotary plate and of the photogrammetrically marked posts 16 in addition to the body of the customer, the upper measuring head 17 substantially detecting the upper parts of the body and not detecting the occluded parts such as, e.g., the lower belly, and the lower measuring head 18 substantially detecting the lower parts of the body and the occluded parts that are not visible to the upper measuring head 17;

(2) the two vertical posts 16 with the holding bow 15, which according to the invention are marked with two different types of marks:

a. with absolutely encoded, photogrammetrically evaluatable marks 31, b. with free surfaces 19 that are not encoded.

FIG. 2 shows a further configuration of the encoded posts 16 in which both those parts of the posts 16 that are located below the holding bow 15 are encoded and also two further parts of the posts 16, protruding into the upper measuring space, are marked and encoded in the same way. Advantageously arranged marked surfaces are thereby produced for the inherent self-calibration according to the invention, in particular of the upper measuring head 17.

FIG. 3 shows a fine-screen illustration in detail, in black-and-white due to the printing process, of the configuration of the marking according to the invention, both of the rotary plate 12 and of the vertical posts 16. Two projected light lines of the measuring head are visible, the line 32 of the first line projector L1 of the measuring head brightly marking essentially the right leg and the lower belly in this exposure, and the line 33 of the second line projector L2 of the measuring head marking the calf/foot region of the left leg and also leaving a well visible line trace on the free field 19 of the post 16.

The photogrammetric markings 31 of the rotary plate define the XY base area of the world coordinate system of the scanner. They are detected by the camera during rotation of the customer together with the light line traces in each image taken and, as is known to those skilled in the art of photogrammetry, thus allow the internal and external parameters of the camera to be automatically determined. In addition, they constitute an absolute scale for converting lateral deflections of the line traces to distance data and the automatic preparation therefrom of a calibrated 3D model of the scanned body. In this way, an inherent self-calibration of the camera and its mounting is achieved, but not the calibration of the complete measuring head which, as shown by way of example in FIG. 4, comprises a camera K and a pair of line projectors L1 and L2 symmetrically arranged at a base distance d and oriented at a predefined triangulation angle in relation to the optical axis of the camera. This arrangement does not yet allow information to be obtained in respect of the calibration of the entire measuring head, i.e. in respect of the automatic determination of the internal and external parameters of the entire measuring head.

In one example, as shown in FIG. 3, for this purpose the marking of the rotary plate is interrupted by a mark-free surface 19 at several locations as an example; the marking of the posts 16 is also interrupted by such a mark-free surface 19. As will be discussed below, these mark-free surfaces 19 on the rotary plate 12 and on the posts 16 serve for the inherent self-calibration of the entire measuring setup in a manner according to the invention, the measuring setup comprising cameras, line projectors, and mechanical structures inclusive of the (marked) posts.

This fundamental concept of the invention will be discussed in more detail with reference to the sketch of FIG. 4. In order to calibrate the measuring head 18 comprising a line projector and a camera, for example, all of the internal and external parameters not only of the camera, but of the entire measuring head need to be able to be photogrammetrically calculated with the aid of the images prepared during the rotation process.

The determination of the internal and external parameters of the camera may be effected in a known manner from the sequence of the images taken during the rotation process since the marked rotary plate is visible at least partly in each image taken.

In one example, the external and internal parameters of the line projector(s) are determined in that in numerous images taken during the rotational movement, the line-type light traces of the line projectors are evaluated on the basis of the unmarked partial surfaces 19 on the rotary plate and the unmarked partial surfaces 19 on the posts 16.

The course of the light trace on an unmarked field of the rotary plate 12 allows the triangulation angle between the camera and the projected light plane in the XY-plane to be derived, i.e. with reference to the base area of the world coordinate system XYZ.

The course of the light trace on an unmarked field of the posts 16 allows the cant of the line projector to be determined, i.e. the angle of rotation in the ZX-plane.

However, to this end the positions in space of the unmarked surfaces of the posts need to be known. This can be done by a strictly vertical orientation along the Z-axis, for example. But such a requirement is contradictory to the objective of obtaining a low-cost scanner having an only moderately robust and constant mechanical design.

Therefore, according to the invention the position(s) in space of this/these non-marked surface(s) is/are established photogrammetrically from the images of the camera during the rotation process with the aid of the absolute markings 31 (see FIG. 3) of the posts 16, so that the entire holding structure comprising the holding bow 15 and the posts 16 likewise need not be mechanically designed so as to be precise and constant, but its precision can be photogrammetrically derived from the inherent determination of the spatial position of the non-marked partial surfaces of the posts. A precondition here is that the positions of the marking-free fields relative to the surrounding or adjacent photogrammetric marks are known to the computer, e.g. in the form of a list or table of those marks which are boundary marks for the marking-free fields.

Since the photogrammetric marks are uniquely identified by their individual encodings, the embedded marking-free fields are also uniquely identified. This allows these marking-free fields to be automatically detected in the image of the camera and the geometric course of the at least one light trace of the at least one line projector in the marking-free field or fields to be determined likewise using methods known to those skilled in the art of image processing and photogrammetry.

Figure 3A:
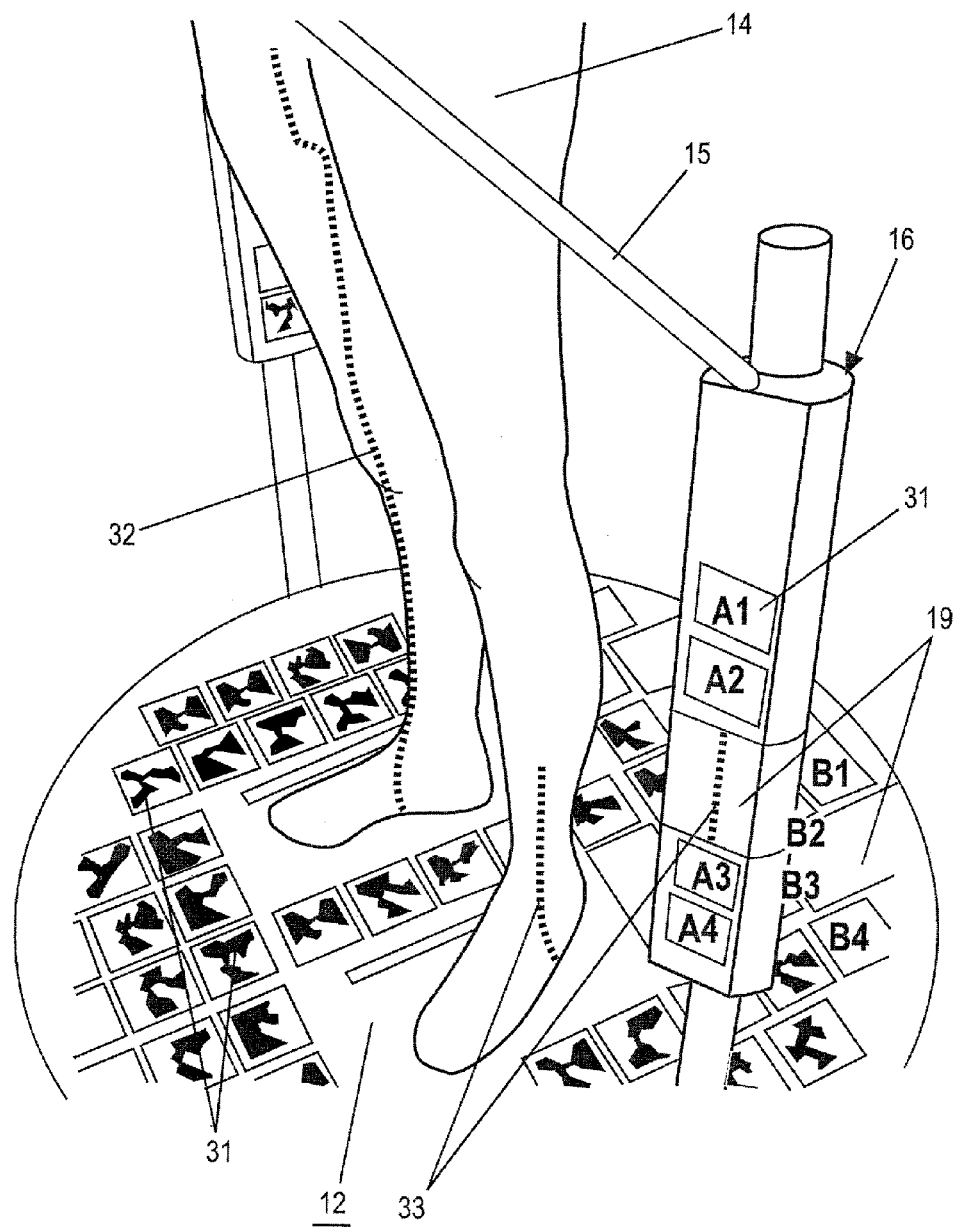
FIG. 3a shows a perspective oblique view to illustrate the positions of marking-free fields relative to surrounding or adjacent photogrammetric marks.

In FIG. 3a, the concept already mentioned in FIG. 3 is more clearly explained graphically. By way of example, two marking-free fields are provided, field A on the vertical post and field B on the horizontal base plate. Field A is framed by the photogrammetric marks A1, A2 (above) and the marks A3, A4 (below). Field B is framed by the marks B1, B2, B3, B4, with the marks B3 and B4 being partly concealed in the illustration by the vertical post. The symbols A and B here stand for the absolutely encoded, graphical photogrammetric marks.

During the rotational movement, all visible photogrammetric marks are recorded in the images respectively captured by the camera. The marking-free fields are also included here. It is not relevant whether the actual photogrammetric evaluation is performed in the evaluation computer already at the same time as the rotational movement or only after a complete scan (which typically includes of 100 images); both options are known in the prior art.

The definition of "shape+location+surrounding photogrammetric marks of the marking-free field" is stored in the evaluation computer for each marking-free field. The definition where the marking-free fields are located, i.e. by which photogrammetric marks they are bordered, must be known to the evaluation computer (e.g. in the form of a list or table of those marks which constitute boundary marks for marking-free fields). The photogrammetric evaluation of all marks provides 3D coordinates, i.e. the 3D position of each mark and thus also the 3D position of each marking-free field. Therefore, after the photogrammetric evaluation, the following have been established: (a) WHERE marking-free fields are located in the world coordinate system (position in space); (b) WHICH marking-free fields are involved (field A, field B, . . . ), as can be determined by means of the indices of the surrounding marks; and (c) thus implicitly also the SHAPE which these fields have (rectangular, square, . . . ). Based on this evaluation, the geometric course (angle related to the XY- or the ZX-coordinate axes) of the light trace of the at least one line projector can then be specifically determined in the marking-free areas or fields (provided that the light trace in the respective image taken meets a marking-free field). Using these two angles, the rotation and the cant of the at least one light line projector in relation to the world coordinate system has been determined, and thus the entire triangulation system, that is, camera+line projector, is inherently calibratable, i.e. within the meaning of this invention it is calibration-free for the user.

Deviations from the rectilinearity of the projected line, for example due to errors or misalignments of the beam shaping optical systems of the line projector, can also be calibrated according to FIG. 6 in that a plurality of sections of the line projected on the largely vertically oriented, mark-free field 61 are detected by the camera or cameras of the measuring head and are described in a known manner by a function, e.g. a polynomial function. This non-linear light section function is then applied in the 3D reconstruction.

As a result, according to the invention the entire mechanical measuring setup and the measuring heads comprising the camera(s) and line projector(s) are inherently self-calibrating, i.e. calibration-free from the point of view of the user:

c. the internal and external parameters of the at least one camera of a measuring head are derived from the observation of the photogrammetric markings of the rotary plate during the rotational movement;

d. the still missing internal and external parameters of the line projectors in the at least one triangulation measuring head are derived from the observation of the course of the light traces of the at least one light line projector in the marking-free fields of the rotary plate and of the posts.

The construction of the scanner can thus be correspondingly light-weight and low-cost, so that the objective according to the invention of providing a whole-body scanner which is both cost-efficient to manufacture and simple to operate without any repeated complicated calibration procedures is attained.

The construction according to FIG. 1 and the design of the triangulation measuring head according to FIG. 4 should be understand merely as examples. The concept of the invention also covers structures having only one triangulation measuring head or having more than two triangulation measuring heads, or with an arrangement of the measuring head or heads different from the one shown, as long as the measuring heads detect both the photogrammetrically marked and the marking-free fields of the rotary plate and of the posts during the scanning process.

The attachment of the vertically applied marking fields to the posts 16 is to be understood to be exemplary. Arrangements in which these fields are applied separately from a holding device and move with the rotary plate are covered by the concept of the invention.

In one example, in the case of measuring heads having more than one line projector or when using a plurality of measuring heads each with one or more line projectors, these projectors are operated either in spectral or time-division multiplexing for better assignment of their light traces to the camera images.

"Spectral multiplexing" is understood to mean the requirement that each projector emits a line with a different primary color in the spectral region of the camera sensitivity. The use of a color-capable camera thus allows the traces of different line projectors to be distinguished with the aid of the respectively different color.

Within the scope of this invention, "spectral multiplexing" is also understood to mean the fact that the different line projectors each emit in a respectively different wavelength range, and the cameras of the individual measuring heads are sensitive only to the light line of one projector, each with the aid of an optical band-pass filter. This allows, for example, the light traces of the upper measuring head 17 from FIG. 1 to be separated in a simple manner from those of the lower measuring head 18 in the overlap area of the cameras of the two measuring heads.

Within the scope of this invention, "time-division multiplexing" is understood to mean the fact that the different line projectors are operated only for short periods of time in a pulsed fashion for different image recordings of the camera, so that the light traces generated by the individual line projectors will not overlap in an image of the camera.

Those of ordinary skill in the art of image processing are familiar with combining spectral and time-division multiplexing arrangements in order to obtain the best trade-off between the simultaneous emission of as many light lines as possible and the error-free assignment of these light lines to the individual projectors from the images of the camera.

Owing to the freedom from calibration, the scanner according to the invention can also be easily modularly expanded. For instance, the low-cost basic variant may include only one single measuring head, which covers a limited measuring space from the feet up to the waist. A later expansion by mounting a further measuring head is easy to carry out since because of the self-calibration no precise orientations or lens settings etc. to be ensured by design measures are required. As a result, the requirements of a highly modular, easily expandable 3D measuring system are met.

In one example, the 3D body scanner is extended by additional sensors and signal generators to form a so-called multisensorial system which, in addition to the 3D spatial shape, generates additional medically-diagnostically interesting information and/or injects stimuli into the body for therapy. To this end, the entire structure is already prepared to receive additional sensors and the software is configured to incorporate the respective add-on programs.

This concept of the invention will be set forth more clearly by way of example provided by the following non-exclusive list of additional modules and measurements:

1. in addition to the spatial shape, the body weight can be determined with or weighing cells adapted to be retrofitted in chambers prepared in the rotary plate;

2. the position of equilibrium of the standing customer is determined with scales or a pressure sensor that is separate for each foot;

3. the sole imprint images of the feet of the customer are determined with integrated space-resolved pressure sensors and thus important data for the manufacture of an anatomically fitting arch support is provided;

4. the percentage of body fat is approximately determined with electrodynamic field electrodes on the soles of the feet;

5. the pulse is measured by hand electrodes on the holding bow;

6. the percentage of body fat is measured electrodynamically by hand and foot electrodes;

7. actively switchable light-emitting sources are built into the rotary plate in the foot position and/or into the holding bow in the hand position for diagnostic purposes, which couple spectrally matched light into the body of the customer via the sole of the foot or via the hands; the luminous effects produced in the hands and legs are observed with the camera or cameras of the measuring head or heads in order to detect medical-diagnostic statements about blood circulation, tissue density, condition of arteries and veins and the like;

8. a color image useful for dermatological purposes is generated in addition to the 3D model by color cameras that can be additionally retrofitted into a holder prepared therefor and is represented separately or superposed with respect to the model;

9. in addition to the course of the light lines on the body surface, the lateral light scatter (the halation around the line) is also measured by the available cameras of the measuring heads and is detected as a measure of local, medically relevant special features such as scarring, skin lichens and skin tumors, fluid accumulations near the skin, and medically relevant special features similarly expressing themselves in the local light scatter;

10. diagnostically relevant thermal images are obtained with an additional thermal imaging camera and are displayed separately or so as to be superimposed on the 3D model;

11. one or more motion detectors integrated in the rotary plate and/or in the holding bow recognize whether the customer has moved in an inadmissible fashion during rotation of the rotary plate, thus producing an unusable data set, so that the scanning process can be aborted;

12. upon an abortion as mentioned sub 11. above, a marking is generated in the 3D data set by a control program, and in the later reconstruction of the entire 3D model the individual views are reconstructed only in those sections which corresponds to a motionless scanning, and these separate partial views are fitted in to form a complete 3D model in a second step.

In one example, not only are sensors retrofitted, but physical signals or stimuli are actively fed into the body of the customer to be scanned, in order to derive medically/diagnostically interesting data in addition to the three-dimensional shape. In this case, too, according to the invention these actuators are adapted to be modularly retrofitted. By way of example, the following active signal injections are mentioned:

13. low-frequency pulsed magnetic fields for the treatment of arthrosis and bone healing are injected by coils integrated in the rotary plate or in the holding bow;

14. medium-frequency mechanical vibration signals for muscle training, for the treatment of tinnitus, etc. are injected by means of coils integrated in the rotary plate or in the holding bow.

Accordingly, in addition to a particularly cost-efficient and easily operable, calibration-free 3D body or body part scanner, the concept of the invention comprises the modular expansion thereof to form a multisensorial measuring and diagnosis and therapy station, with the possibility of medically/diagnostically useful data that is separate or superimposed on the three-dimensional shape.

Although an embodiment of this invention has been disclosed, a worker of ordinary skill in this art would recognize that certain modifications would come within the scope of this invention. For that reason, the following claims should be studied to determine the true scope and content of this invention.

The invention claimed is:

1. A method for cost-efficient and precise optical detection of a three-dimensional shape of a body or a part of the body according to a light section procedure, the method comprising the following steps:
(a) providing a self-calibrating detection device comprising:
a support plate with a horizontal flat surface,
a substantially vertical structure,
at least one stationary triangulation measuring head including at least one camera and at least one light line projection, and
a computer;
(b) arranging at least one marking-free field on the support plate and at least one marking-free field on the substantially vertical structure;
(c) arranging encoded, photogrammetrically evaluatable marks on the support plate around the standing surface and on the substantially vertical structure;
(d) storing, in the computer, positions of the marking-free fields relative to the surrounding or adjacent photogrammetrically evaluatable marks;
(e) rotating the support plate with the horizontal flat standing surface and the at least one substantially vertical structure about a vertical axis while the body stands upright on the standing surface of the support plate;
(f) projecting light lines onto the body and the marking-free fields the at least one light line projector to provide light traces on the marking-free fields, and wherein the light lines are substantially perpendicular to a plane of the support plate;
(g) taking, with the camera during rotation of the support plate, images of the body or part of the body, the photogrammetrically evaluatable marks, and the light traces on the marking-free fields;
(h) transferring the images taken by the camera during rotation of the support plate to the computer
(i) determining, with the computer, a position space for the marking-free fields based on the positions of the photogrammetrically evaluatable marks and the stored positions of the marking-free field relative to the surrounding or adjacent photogrammetrically evaluatable marks;
(j) based on the positions of the photogrammetrically evaluatable marks and positions and shapes of light traces on the marking-free fields, the computer determines parameters of the triangulation measuring head and performs a self-calibration of the detection device; and
(k) determining, with the computer, a three-dimensional shape of the body or part of the body using the transferred images and photogrammetric program.

2. The method according to claim 1, wherein a plurality of triangulation measuring heads cover a measuring space from the support plate up to at least a highest body point to be detected, each with an overlap, and orientating each triangulation measuring head such that the triangulation measuring head detects at least part of the marks of the support plate and of the substantially vertical structure.

3. The method according to claim 2, wherein emitting the line projectors of the plurality of triangulation measuring heads in different spectral regions, and connecting an optical filter upstream of the respectively associated camera, the optical filter transmitting light only from this spectral region.

4. The method according to claim 2, wherein emitting the line projectors of the plurality of triangulation measuring heads in different spectral regions, and wherein the respectively associated camera is color-capable and the computer executes a color classification program which allocates the light traces of the individual line projectors in the image of the color camera to the line projectors.

5. The method according to claim 1, wherein signals generated by the body or part of the body are detected using sensors built into the support plate and/or the holding device, and are evaluated by the computer.

6. The method according to any of claim 1, wherein physical stimuli perceptible by the body or part of the body are generated by using actuators built into the support plate and/or the holding device.

7. The method according to claim 1, wherein the at least one marking-free field comprises a plurality of marking-free fields arranged on the support plate, and including arranging the plurality of marking-free fields to be interspersed with the encoded, photogrammetrically evaluatable marks on the support plate.

8. The method according to claim 1, wherein the at least one marking-free field on the substantially vertical structure comprises a plurality of marking-free fields on the substantially vertical structure, and including arranging the plurality of marking-free fields to be interspersed with the encoded, photogrammetrically evaluatable marks on the substantially vertical structure.

9. The method according to claim 1, wherein the at least one marking-free field for the support plate and for the substantially vertical structure is defined by boundary marks.

10. The method according to claim 1, wherein
the at least one marking-free field for the support plate comprises a first plurality of marking-free fields arranged on the support plate, and including arranging the first plurality of marking-free fields to be interspersed with the encoded, photogrammetrically evaluatable marks on the support plate,
the at least one marking-free field on the substantially vertical structure comprises a second plurality of marking-free fields on the substantially vertical structure, and including arranging the plurality of marking-free fields to be interspersed with the encoded, photogrammetrically evaluatable marks on the substantially vertical structure, and
the marking-free fields for the support plate and for the substantially vertical structure are defined by boundary marks.

11. The method according to claim 1, wherein the at least one stationary triangulation measuring head comprises only an upper measuring head and a lower measuring head positioned vertically below the upper measuring head, and wherein the upper measuring head substantially detects upper portions of the body or part of the body and the lower measuring head substantially detects lower portions of the body or part of the body that are not visible to upper measuring head.

12. A self-calibrating detection device for calibration-free, cost-efficient and precise optical detection of the three-dimensional shape of a body or a part of the body according to a light section procedure, the device comprising:

(a) a support plate that is rotatable about a vertical axis and on which a horizontal flat standing surface is formed and which carries at least one substantially vertical structure connected with the support plate;
b) encoded, photogrammetrically evaluatable marks arranged on the support plate around the standing surface and on the at least one substantially vertical structure;
(c) at least one marking-free field arranged on the support plate and at least one marking-free field arranged on the substantially vertical structure;
(d) at least one stationary triangulation measuring head including at least one light line projector configured to project light lines that are substantially perpendicular to a plane of the support plate onto the body or the part of the body that stands upright on the standing surface of the support plate, thereby providing light traces on the marking-free fields, and at least one camera configured to take images of the body or part of the body, the photogrammetrically evaluatable marks, and the light traces on the marking-free fields during rotation of the support plate;
(e) a computer having stored thereon positions of the marking-free fields relative to the surrounding or adjacent photogrammetrically evaluatable marks, the computer configured to
(i) receive the images taken by the camera during rotation of the support plate;
(ii) determine a position in space for the marking-free fields based on the positions of the photogrammetrically evaluatable marks and the stored positions of the marking-free fields relative to the surrounding or adjacent photogrammetrically evaluatable marks;
(iii) based on the positions of the photogrammetrically evaluatable marks and the positions and shapes of the light traces on the marking-free fields, determine parameters of the triangulation measuring head and perform a self-calibration of the detection device; and
(iv) photogrammetrically determine a three-dimensional shape of the body or part of the body using the received images.

13. The detection device according to claim 12, wherein the vertical structure is part of a holding device for the body or part of the body to hold on to during the rotation of the support plate.

14. The detection device according to claim 12, wherein the support plate is adapted to be rotated by a motor.

15. The detection device according to claim 12, wherein the support plate is adapted to be rotated manually.

16. The detection device according to claim 12, wherein a plurality of triangulation measuring heads are provided that cover a measuring space from the support plate up to at least a highest body point to be detected, each with an overlap, the line projectors of the plurality of triangulation measuring heads emitting in different spectral regions, and either an optical filter being connected upstream of the respectively associated camera, the optical filter transmitting light only from this spectral region, or the respectively associated camera being color-capable and the computer executing a color classification program which allocates the light traces of the individual line projectors in the image of the color camera to the line projectors.

17. The detection device according to claim 12, wherein sensors for electronically detecting signals that are generated by the body or part of the body and which can be evaluated by the computer and/or actuators adapted to generate physical stimuli perceptible by the body or part of the body are built into the support plate and/or the holding device.

18. The detection device according to claim 12, wherein the at least one marking-free field comprises a plurality of marking-free fields arranged on the support plate, wherein the plurality of marking-free fields are interspersed with the encoded, photogrammetrically evaluatable marks on the support plate.

19. The detection device according to claim 12, wherein the at least one marking-free field on the substantially vertical structure comprises a plurality of marking-free fields on the substantially vertical structure, and wherein the plurality of marking-free fields are interspersed with the encoded, photogrammetrically evaluatable marks on the substantially vertical structure.

20. The detection device according to claim 12, wherein the at least one marking-free field for the support plate and for the substantially vertical structure is defined by boundary marks.

21. The detection device according to claim 12, wherein
the at least one marking-free field for the support plate comprises a first plurality of marking-free fields arranged on the support plate, wherein the first plurality of marking-free fields are interspersed with the encoded, photogrammetrically evaluatable marks on the support plate,
the at least one marking-free field on the substantially vertical structure comprises a second plurality of marking-free fields on the substantially vertical structure, and wherein the plurality of marking-free fields are interspersed with the encoded, photogrammetrically evaluatable marks on the substantially vertical structure, and
wherein the marking-free fields for the support plate and for the substantially vertical structure are defined by boundary marks.

22. The detection device according to claim 12, wherein the at least one stationary triangulation measuring head comprises only an upper measuring head and a lower measuring head positioned vertically below the upper measuring head, and wherein the upper measuring head substantially detects upper parts of the body or part of the body and the lower measuring head substantially detects lower portions of the body or part of the body that are not visible to upper measuring head.

\* \* \* \* \*